US012046339B1

(12) United States Patent
Bhandaru et al.

(10) Patent No.: US 12,046,339 B1
(45) Date of Patent: Jul. 23, 2024

(54) APPARATUS, SYSTEM AND METHOD FOR PROCESSING AND SECURING PRESCRIPTION DATA IN A COMPUTER SYSTEM

(71) Applicant: ALLSCRIPTS SOFTWARE, LLC, Chicago, IL (US)

(72) Inventors: Ramakant Bhandaru, Chester Springs, PA (US); Matthew David Dreselly Thomas, Atlanta, GA (US)

(73) Assignee: Allscripts Software, LLC, Chicago, IL (US)

( * ) Notice: Subject to any disclaimer, the term of this patent is extended or adjusted under 35 U.S.C. 154(b) by 217 days.

(21) Appl. No.: 16/542,998

(22) Filed: Aug. 16, 2019

(51) Int. Cl.
G16H 20/10 (2018.01)
H04L 9/32 (2006.01)
H04W 12/06 (2021.01)
G16H 10/60 (2018.01)

(52) U.S. Cl.
CPC .......... *G16H 20/10* (2018.01); *H04L 9/3228* (2013.01); *H04W 12/06* (2013.01); *G16H 10/60* (2018.01)

(58) Field of Classification Search
None
See application file for complete search history.

(56) References Cited

U.S. PATENT DOCUMENTS

| 7,706,915 | B2 * | 4/2010 | Mohapatra | G16H 20/10 700/242 |
| 10,395,014 | B2 * | 8/2019 | Giatilis | G06F 21/31 |
| 2008/0015897 | A1 * | 1/2008 | Moradi | G16H 20/13 705/2 |
| 2013/0297333 | A1 * | 11/2013 | Timmons | G16H 20/10 705/2 |

(Continued)

FOREIGN PATENT DOCUMENTS

JP    2002288343 A  * 10/2002

OTHER PUBLICATIONS

M. A. Sadikin and S. U. Sunaringtyas, "Implementing digital signature for the secure electronic prescription using QR-code based on Android smartphone," 2016 International Seminar on Application for Technology of Information and Communication (ISemantic), Semarang, Indonesia, 2016, pp. 306-311 (Year: 2016).*

(Continued)

*Primary Examiner* — Rachel L. Porter
(74) *Attorney, Agent, or Firm* — Peter Zura; LOZA & LOZA, LLP (57) ABSTRACT

Technologies and techniques for securing prescription data on a computer network. A prescription module is activated for registering prescription data. An authentication module is activated, where an entry field is disabled in the prescription application to register the prescription data for a predetermined period of time. While the entry field is disabled, the authentication module determines if the prescription application is active, and the entry field in the prescription (Continued)

application is activated only after the predetermined period of time has lapsed, and when the prescription application was determined to be active for the predetermined period of time. A soft token that is not received on the device, may then be entered to authenticate the prescription data.

18 Claims, 8 Drawing Sheets

(56) References Cited

U.S. PATENT DOCUMENTS

2017/0213010 A1* 7/2017 Sucilla ................ H04L 9/3226
2020/0210988 A1* 7/2020 Woodward ........... G06Q 20/409

OTHER PUBLICATIONS

Chadwick, David W. and Mundy, Darren (2004) The Secure Electronic Transfer of Prescriptions. In: Bryant, Jacqueline, ed. Current Perspectives in Healthcare Computing Conference. BCS HIC, pp. 11-28. ISBN 978-0-9546971-0-5 (Year: 2004) Abstract citation.*
Chadwick, David W. and Mundy, Darren (2004) The Secure Electronic Transfer of Prescriptions. In: Bryant, Jacqueline, ed. Current Perspectives in Healthcare Computing Conference. BCS HIC, pp. 11-28. ISBN 978-0-9546971-0-5 (Year: 2004)—full document.*

* cited by examiner

APPARATUS, SYSTEM AND METHOD FOR PROCESSING AND SECURING PRESCRIPTION DATA IN A COMPUTER SYSTEM

FIELD OF TECHNOLOGY

The present disclosure is directed to technologies and techniques for processing medical data in a computer system. More specifically, the present disclosure is directed to authentication techniques in a medical software environment.

BACKGROUND

Medical software technology has advanced through the years to allow health care providers to monitor and improve the health care services provided to patients. Unlike conventional generic software systems, medical software technology must be specifically configured to process medical codes and provide ample security for patient data. Practice management software (PM) has been developed to manage different administrative and clinical aspects of healthcare. This software centralizes various systems so users can run things more efficiently. It automates almost every task that fits under the "health information management" umbrella.

Prescription monitoring programs (PMPs) or prescription drug monitoring programs (PDMPs) are state-run programs that collect and distribute data about the prescription and dispensation of federally controlled substances and other potentially addictive or abusable prescription drugs. PMPs help to prevent adverse drug-related events through opioid overdoses, drug diversion, and substance abuse by decreasing the amount and/or frequency of opioid prescribing. Pharmacies dispensing controlled substances and prescribers are typically required to register with their respective state PMPs and (for pharmacies and providers who dispense controlled substances from their offices) to report the dispensation of such prescriptions to an electronic online database.

The Drug Enforcement Administration allows for the e-prescribing of controlled substances under the Electronic Prescriptions for Controlled Substances (EPCS) interim final rule, where e-prescribing systems rely on strong security features to prevent doctor shoppers and abuse of schedule II, III and IV controlled substances, and to ensure that only an authorized prescriber is issuing prescriptions. Some of the strongest security features in these technologies include identity proofing and two-factor authentication, and both play a key role in e-prescribing. Identity proofing is a process of issuing credentials to users that relies on the physician or prescriber to provide and verify information that would be known only to the physician, both when requesting credentials to access the system, and when using those credentials to access the system. The process may ask for personally identifiable information known only to the individual in order to validate the person's identity. Common questions asked as part of identity proofing are for the mother's maiden name and the last four digits of the Social Security number.

Two-factor authentication is essentially the requirement that the physician possess and use two distinct elements in order to gain access to the e-prescribing tool. For example, the physician may enter a username and password into an e-prescribing software tool. Before granting access, the e-prescribing system might send a text with an access code to the cell phone of the physician. In order to gain access to the system, the physician would then enter the one-time use code from the text message. In order to compromise access, someone would need to have access to both the provider's user identification and password and the mobile phone of the provider.

Technologies directed to two-factor authentication include hardware tokens ("hard" tokens) and software tokens ("soft" tokens). With a software token, the one-time password (OTP) application or PKI certificate isn't stored on a device specifically designed to secure such sensitive data. Instead, it's downloaded and stored on any average computing device such as a mobile phone, tablet, or desktop. As a result, the token is "soft" because it isn't tied to a particular hardware device. Hard tokens, on the other hand, involve two things: the OTP application or PKI certificate itself and the hardware device it's stored on. The two can't be separated. With a hard token, the information is kept within that single device, which is designed to keep the information inside secure.

While hard tokens may be more secure in certain applications, hard tokens require the end users to purchase additional hardware, which drives up costs. Accordingly, the industry has begun moving more towards soft tokens, such as ID.me and others that are capable of creating Identity Assurance Level 2 (IAL2) and Level of Assurance 3 (LOA3) credentials compliant credentials that can be used by patients and providers across healthcare systems. However, further improvements are needed to increase the level of security, particularly for soft tokens.

SUMMARY

Various apparatus, systems and methods are disclosed herein relating to specialized computer systems for drug data processing and image data processing.

In some illustrative embodiments, systems and apparatuses are disclosed for processing and securing prescription data on a computer network, comprising: a processor; a memory, operatively coupled to the processor; a communications interface, operatively coupled to the processor, wherein the communications interface is configured to communicate with the computer network; a prescription module, operatively coupled to the processor, wherein the prescription module is configured to operate a prescription application to register prescription data; and an authentication module, operatively coupled to the processor, wherein the authentication module is configured to disable an entry field in the prescription application, for a predetermined period of time, to register the prescription data, determine, while the entry field is disabled, if the prescription application is active, activate the entry field in the prescription application after the predetermined period of time has lapsed, and the prescription application was determined to be active, receive entry of a one time password in the entry field, wherein the one time password is based on a code transmitted to a device other than the apparatus, and authenticate the registered prescription data.

In some illustrative embodiments, methods are disclosed for securing prescription data on a computer network, comprising: activating a prescription module, via a processor, for registering prescription data; activating an authentication module, via the processor; disabling, via the authentication module, an entry field in the prescription application to register the prescription data, for a predetermined period of time; determining, via the authentication module, while the entry field is disabled, if the prescription application is active; activating, via the authentication module, the entry field in the prescription application after the predetermined period of time has lapsed, when the prescription application was determined to be active for the predetermined period of time; receiving in the authentication module entry of a one time password in the entry field, wherein the one time password is based on a code transmitted to a device not containing the authentication module, and authenticating, via the authentication module the registered prescription data.

In some illustrative embodiments, methods are disclosed for securing prescription data on a computer network, comprising: activating a prescription module, via a processor, for registering prescription data; activating an authentication module, via the processor; disabling, via the authentication module, an entry field in the prescription application to register the prescription data, for a predetermined period of time; determining, via the authentication module, while the entry field is disabled, if the prescription application is active; activating, via the authentication module, the entry field in the prescription application after the predetermined period of time has lapsed, when the prescription application was determined to be active for the predetermined period of time; receiving in the authentication module entry of a one time password in the entry field, wherein the one time password is based on a soft token code transmitted to a device not containing the authentication module, and authenticating, via the authentication module the registered prescription data.

BRIEF DESCRIPTION OF THE FIGURES

The present invention is illustrated by way of example and not limitation in the figures of the accompanying drawings, in which like references indicate similar elements and in which.

DETAILED DESCRIPTION

Various embodiments will be described herein below with reference to the accompanying drawings. In the following description, well-known functions or constructions are not described in detail since they may obscure the invention in unnecessary detail.

It will be understood that the structural and algorithmic embodiments as used herein does not limit the functionality to particular structures or algorithms, but may include any number of tangibly-embodied software and/or hardware components. In general, a computer program product in accordance with one embodiment comprises a tangible computer usable medium (e.g., hard drive, standard RAM, an optical disc, a USB drive, or the like) having computer-readable program code embodied therein, wherein the computer-readable program code is adapted to be executed by a processor (working in connection with an operating system) to implement one or more functions and methods as described below. In this regard, the program code may be implemented in any desired language, and may be implemented as machine code, assembly code, byte code, interpretable source code or the like (e.g., via C, C++, C#, Java, Actionscript, Swift, Objective-C, Javascript, CSS, XML, etc.). Furthermore, the term "information" as used herein is to be understood as meaning digital information and/or digital data, and that the term "information" and "data" are to be interpreted as synonymous.

In addition, while conventional hardware components may be utilized as a baseline for the apparatuses and systems disclosed herein, those skilled in the art will recognize that the programming techniques and hardware arrangements disclosed herein, embodied on tangible mediums, are configured to transform the conventional hardware components into new machines that operate more securely and/or efficiently (e.g., providing greater and/or more robust data, while using less processing overhead and/or power consumption) and/or provide improved user workspaces and/or toolbars for human-machine interaction.

Figure 1:
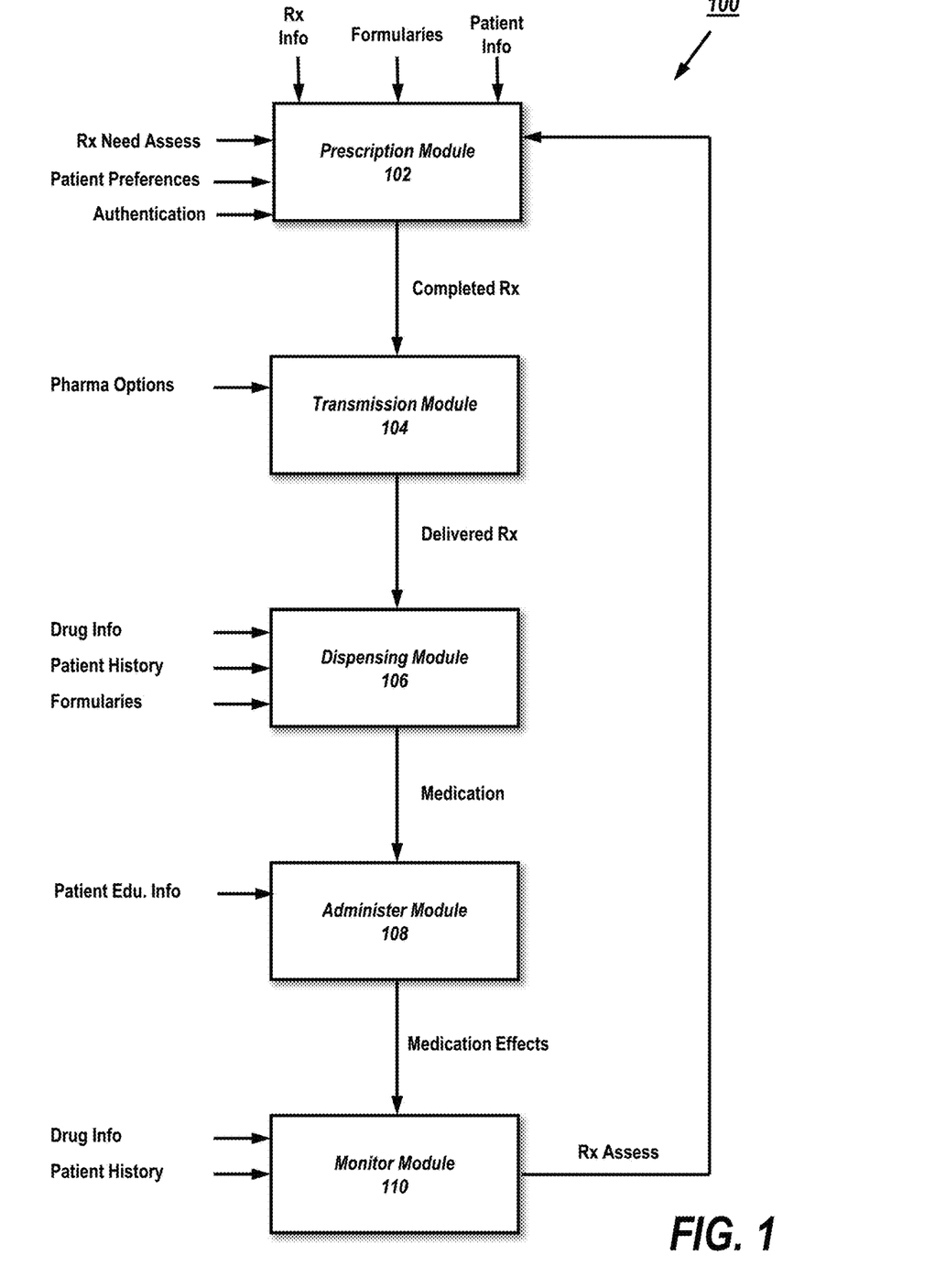
FIG. 1 illustrates a simplified block diagram of a processor-based computer system configured to perform medical data processing, medication management and security under an illustrative embodiment.

Turning to FIG. 1, the drawing illustrates a simplified block diagram of a processor-based computer system 100 configured to perform medical data processing, medication management and security under an illustrative embodiment. The computer system 100 may be embodied in a single server, or may be embodied among multiple servers, including a cloud network under some illustrative embodiments. The computer system may be configured using an electronic prescribing ("e-prescribing") platform, and may utilize function modeling methodologies, including functional modeling languages for the data analysis, development, reengineering, and integration of information systems, business processes; or software engineering analysis. In one example, the computer system 100 may utilize IDEF0 ("Icam DEFinition for Function Modeling"), where IDEF0 is part of the IDEF family of modeling languages in the field of software engineering, and is built on the functional modeling language Structured Analysis and Design Technique (SADT).

As is shown in the figure, prescription module 102 may be configured to receive or load as inputs medical data including, but not limited to, patient preferences, prescription need assessment, prescription information, formularies data, and patient information. The data for prescription module 102 may be provided by a prescribing clinician database, as well as components from an e-prescribing system. Prescription need assessment data comprises data relating to a clinician's assessments about the need for prescription medications. Data relating to the patient's preferences regarding medications as well as drug information, patient data (e.g., known allergies), and drug formulary restrictions, are also processed in prescription module 102. The prescription module 102 also receives an authentication input, which is described in greater detail below, allowing the prescription module to execute prescriptions relating to controlled substances. The output of prescription module 102 comprises a completed prescription, as shown in the figure and may also include output information instructing patient adherence to the prescribed regimen.

After processing this data, prescription module 102 provides a completed prescription to transmission module 104. Using pharmacy option data input that is entered and/or loaded, transmission module transmits delivered prescription data to dispensing module 106, which further process the data, along with data inputs including, but not limited to, drug information, patient history and formulary data. In some illustrative embodiments, problematic prescriptions may be identified in the dispensing module 106 using the techniques described herein, and may be changed or cancelled rather than being dispensed. The administer module 108 may include a patient education information data input as shown an outputs medication effects to monitor module 110, which may include a clinician input of drug information and patient history, where monitor module may output a prescription assessment that may be fed back to prescription module 102 for processing and use during subsequent prescription processes. It should be understood by those skilled in the art that the modules 102-110 of computer system 100 may be combined in various forms, depending on the application, and may include additional modules, depending on the specific application.

Figure 2:
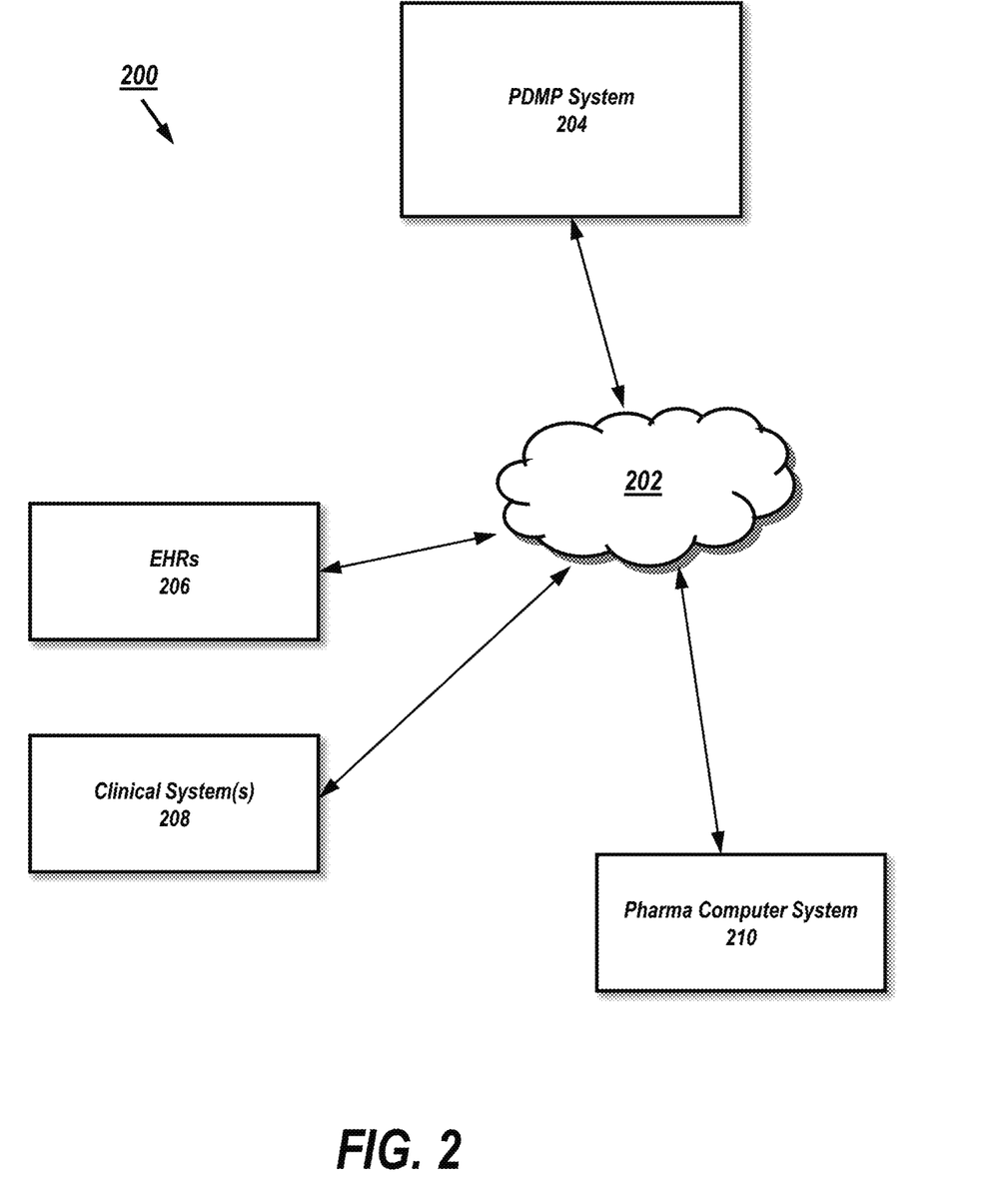
FIG. 2 shows a simplified block diagram of a Prescription Drug Monitoring Program (PDMP) computer system and authentication under an illustrative embodiment.

FIG. 2 shows a simplified block diagram of a Prescription Drug Monitoring Program (PDMP) network system 200 under an illustrative embodiment. In this example, a PDMP system 204 (e.g., PMP AWARxE) is communicatively coupled to a computer network 202, which in turn is communicatively coupled to Electronic Health Record (EHR) system 206, one or more clinical systems 208 and pharmacy computer system 210. In some illustrative embodiments, one or more portions of the PDMP network system 200 may be configured to operate under the U.S. Meds Prescription Drug Monitoring Program FHIR Implementation Guide (US Meds PDMP FHIR IG), where one or more portions of PDMP data may be accessed using the Health Level-7 Fast Healthcare Interoperability Resources (HL7 FHIR) standard. In some illustrative embodiments, other standards may be combined or substituted with the HL7 FHIR standard.

The one or more clinical systems 208 may obtain PDMP data for processing. Each clinical system 208 may comprise a plurality of devices configured to communicate with each other and with the network 202, as well as other devices that may be coupled to the PDMP network system 200. The one or more clinical systems 208 may obtain medical data comprising EHR data from EHR system 206, and may receive pharmaceutical data from pharmacy computer system 210. PDMP data may be obtained from PDMP system 204. In one example, a clinical system (208), using a suitable application (e.g., SMART, FHIR, etc.) may issue a PDMP request, requesting a patient's controlled substance history. In response, the PDMP system accepts the request and transmits a controlled substance history for the patient. The PDMP system 204 may comprise an intermediary system in some illustrative embodiments, where the intermediary system may communicate with a plurality of PDMP systems for obtaining PDMP data. The intermediary system may be configured within a specific system (e.g., clinical system 208), or may be configured as a stand-alone system.

During operation, the clinical system 208 may be configured with an authentication module (e.g., 2-factor authentication) that is specially configured to be linked with a prescription module, wherein entries in the prescription module require a first authentication into the prescription. If the prescription utilizes a controlled substance, the prescription module will require a second authentication utilizing a one-time password (OTP). In some illustrative embodiments, the authentication may be configured such that the OTP cannot be generated/received on the same device that is issuing the prescription. This configuration is typically preferred to mitigate the risk that a single device is improperly authorized to prescribe controlled substances. As will be described in greater detail below, the authentication module may be configured to detect application status and control authentication based on the detected status.

Figure 3:
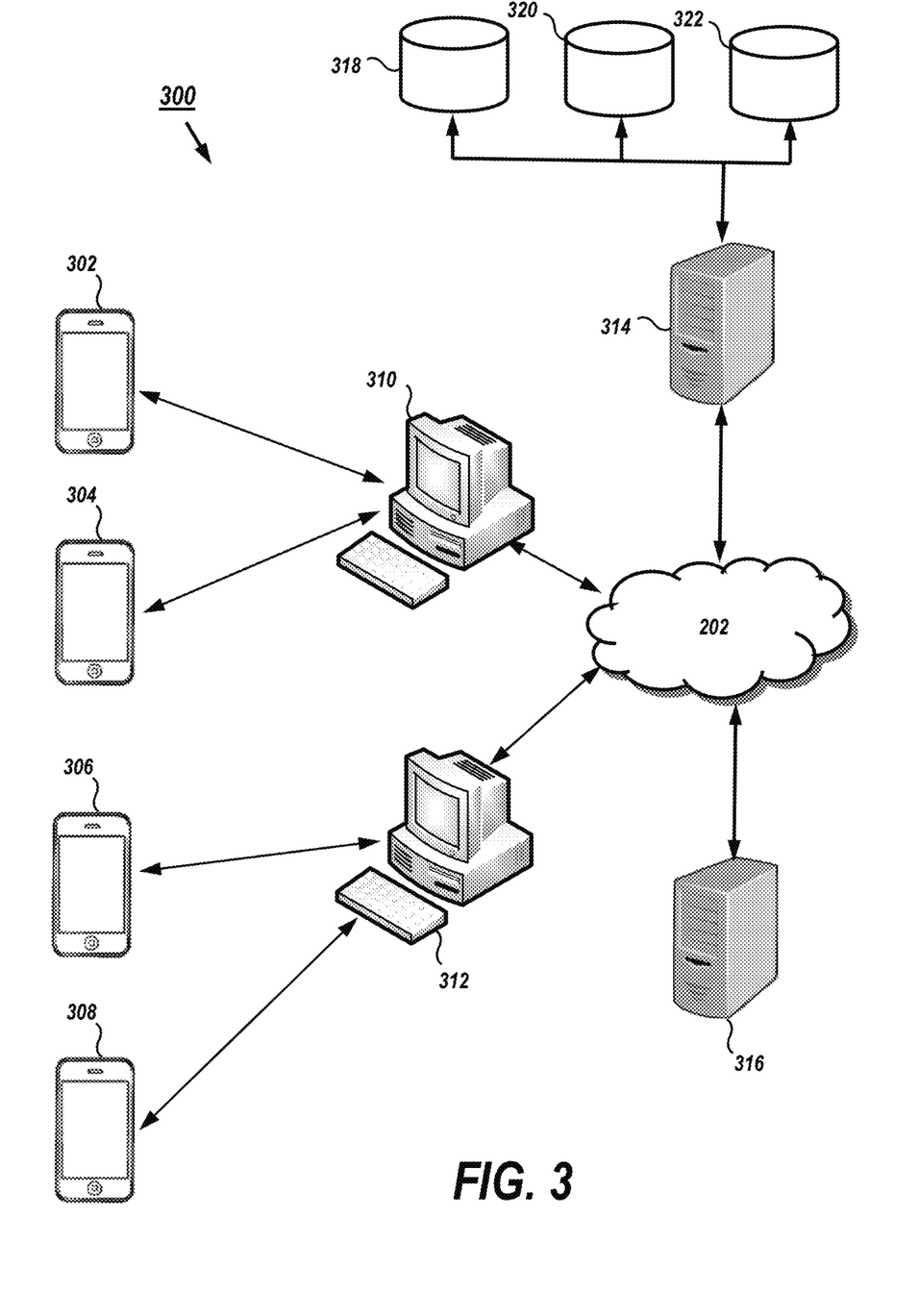
FIG. 3 illustrates a simplified overview of a processor-based computer system configured to perform e-prescription medical data processing and authentication under an illustrative embodiment.

FIG. 3 illustrates a simplified overview of a processor-based computer system 300 configured to perform medical data processing utilizing prescription data an authentication data under an illustrative embodiment. The processor-based computer system 300 may incorporate any and all aspects of the features described above in connection with FIGS. 1-2. The system 300 may include a plurality of portable processing devices 302, 304, 306, 308 and respectively associated computers and/or workstations 310, 312 (computer(s), computing device(s)). Those skilled in the art understand that portable processing devices 302-308 and computers 310-312 may be configured as any suitable device that include, but are not limited to, cell phones, tablets, laptops, personal computers, fitness trackers, workstations, medical processing devices, and the like. Portable processing devices 302-308 and computers 310-312 may communicate with each other via a direct wired or wireless connections (e.g., Bluetooth, Wifi), or through a local network (e.g., LAN).

In one example, portable processing devices 302, 304 may be communicatively coupled to computer 310 and portable processing devices 306, 308 may be communicatively coupled to computer 312. In this example, computers 310, 312 may be computers from different systems (e.g., 408, 410) and may be physically and/or geographically remote from one another. In some illustrative embodiments, computers 310, 312 may be part of the same system (e.g., 408). Computers 310 and/or 312 may be communicatively coupled to a computer network 402, which may be communicatively coupled to a plurality of servers 314, 316. In the example of FIG. 3, server 314 is communicatively coupled with a plurality of databases 318, 320, 322. The databases may be configured as large-scale databases suitable for use in systems, such as EMRs, EHRs, and the like.

Figure 4:
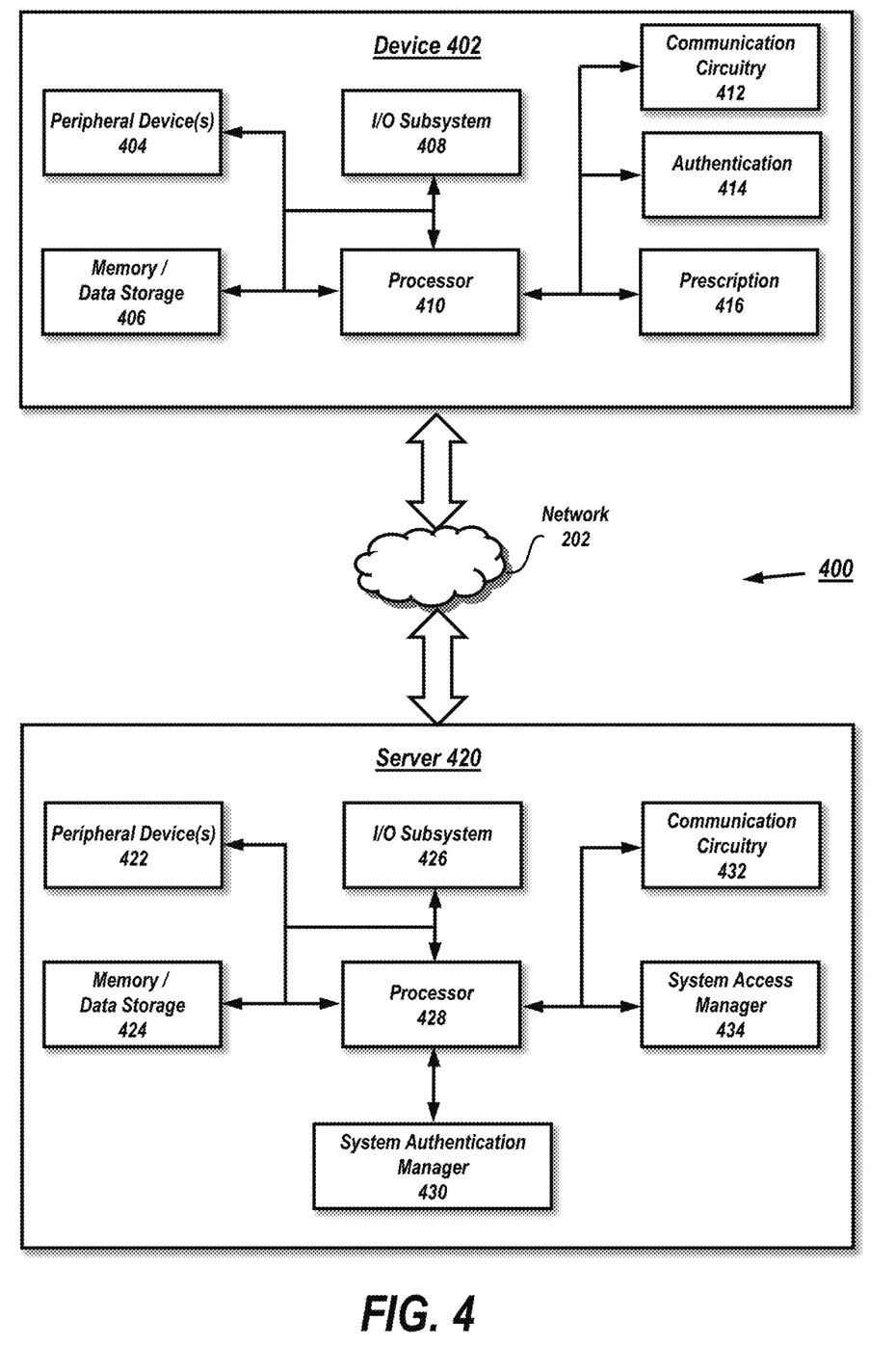
FIG. 4 shows an operating environment for a device and a server in a mobile agent environment for e-prescription medical data processing and authentication under an illustrative embodiment.

FIG. 4 shows an operating environment 400 for system 300 that includes a processing device 402, which may be configured as any of devices 102-108 and/or 108-110, and a server 420, which may be configured as server 114, 116, communicating via the network 112 wherein the operating environment is configured to process medical data including prescription drug data, as explained in greater detail below. In the illustrative embodiment, the processing device 402 includes a processor 410 or processor circuit, one or more peripheral devices 404, memory/data storage 406, communication circuitry 412, input/output (I/O) subsystem, a learning logic module and 414 and mobile agent module 416.

The prescription module 416 of environment 400 may be configured to perform functions pertaining to e-prescribing, including the e-prescribing of controlled substances. Authentication module 414 may be configured to perform aspects of authentication, including, but not limited to, 2-factor authentication. In some illustrative embodiments, prescription module 416 and/or authentication module 414 may be incorporated into memory/data storage 406 with or without a secure memory area, or may be a dedicated component, or incorporated into the processor 410. Of course, processing device 402 may include other or additional components, such as those commonly found in a digital apparatus and/or computer (e.g., sensors, various input/output devices), in other embodiments. Additionally, in some embodiments, one or more of the illustrative components may be incorporated in, or otherwise form a portion of, another component. For example, the memory/data storage 406, or portions thereof, may be incorporated in the processor 410 in some embodiments.

The processor 410 may be embodied as any type of processor currently known or developed in the future and capable of performing the functions described herein. For example, the processor 410 may be embodied as a single or multi-core processor(s), digital signal processor, microcontroller, or other processor or processing/controlling circuit. Similarly, memory/data storage 406 may be embodied as any type of volatile or non-volatile memory or data storage currently known or developed in the future and capable of performing the functions described herein. In operation, memory/data storage 406 may store various data and software used during operation of the processing device 410 such as access permissions, access parameter data, operating systems, applications, programs, libraries, and drivers.

Memory/data storage 406 may be communicatively coupled to the processor 410 via an I/O subsystem 408, which may be embodied as circuitry and/or components to facilitate input/output operations with the processor 410, memory/data storage 406, and other components of the processing device 402. For example, the I/O subsystem 408 may be embodied as, or otherwise include, memory controller hubs, input/output control hubs, firmware devices, communication links (i.e., point-to-point links, bus links, wires, cables, light guides, printed circuit board traces, etc.) and/or other components and subsystems to facilitate the input/output operations. In some embodiments, the I/O subsystem 408 may form a portion of a system-on-a-chip (SoC) and be incorporated, along with the processor 410, memory/data storage 406, and other components of the processing device 402, on a single integrated circuit chip.

The processing device 402 includes communication circuitry 412 (communication interface) that may include any number of devices and circuitry for enabling communications between processing device 402 and one or more other external electronic devices and/or systems. Similarly, peripheral devices 404 may include any number of additional input/output devices, interface devices, and/or other peripheral devices. The peripheral devices 404 may also include a display, along with associated graphics circuitry and, in some embodiments, may further include a keyboard, a mouse, audio processing circuitry (including, e.g., amplification circuitry and one or more speakers), and/or other input/output devices, interface devices, and/or peripheral devices.

The server 420 may be embodied as any suitable server (e.g., a web server, etc.) or similar computing device capable of performing the functions described herein. In the illustrative embodiment of FIG. 2 the server 420 includes a processor 428, an I/O subsystem 426, a memory/data storage 424, communication circuitry 432, and one or more peripheral devices 422. Components of the server 420 may be similar to the corresponding components of the processing device 402, the description of which is applicable to the corresponding components of server 420 and is not repeated herein for the purposes of brevity.

The communication circuitry 432 of the server 420 may include any number of devices and circuitry for enabling communications between the server 420 and the processing device 402. In some embodiments, the server 420 may also include one or more peripheral devices 422. Such peripheral devices 422 may include any number of additional input/output devices, interface devices, and/or other peripheral devices commonly associated with a server or computing device. In some illustrative embodiments, the server 420 also includes system authentication manager 430 and system access manager 434. System authentication manager 430 may be configured to manage authentication for any device (e.g., 402) operatively coupled to the server 420 in operating environment 400. In some illustrative embodiments, system authentication manager 430 does not generate OTPs, but may communicate with 3rd party servers (e.g., authentication service server) providing OTPs to confirm authentication. In some illustrative embodiments, system authentication manager 420 may be configured to generate OTPs and confirm the OTPs on the same sever.

The OTPs may be generated using a suitable algorithm, known in the art. In some illustrative embodiments, the OTP may be based on time-synchronization between an authentication server and the client providing the password, where the OTPs are valid only for a short period of time. In some illustrative embodiments, the OTP may be generated using a mathematical algorithm to generate a new password based on the previous password, where the OTPs are effectively configured as a chain and must be used in a predefined order. In some illustrative embodiments, the OTPs may be generated using a mathematical algorithm where a new password is based on a challenge (e.g., a random number chosen by the authentication server or transaction details) and/or a counter. The OTPs may be configured using software that runs on a user's mobile phone. Alternately or in addition the OTPs may be generated server-side and sent to a user using an out-of-band channel, such as SMS messaging.

System access manager 434 may be configured to manage access credentials for each of devices 420 operatively coupled to the server via network 202. The access credentials include, but are not limited to, access to e-prescribing controlled substances (e.g., via prescription module 416), access to communicate with pharmacy computer system(s) (e.g., 210) as well as access to the operating environment 400 itself.

Continuing with the illustrated embodiment of FIG. 4, communication between the server 420 and the processing device 402 takes place via the network 202 that may be operatively coupled to one or more network switches (not shown). In one embodiment, the network 202 may represent a wired and/or wireless network and may be or include, for example, a local area network (LAN), personal area network (PAN), storage area network (SAN), backbone network, global area network (GAN), wide area network (WAN), or collection of any such computer networks such as an intranet, extranet or the Internet (i.e., a global system of interconnected network upon which various applications or service run including, for example, the World Wide Web). Generally, the communication circuitry of processing device 402 and the communication circuitry 432 of the server 420 may be configured to use any one or more, or combination, of communication protocols to communicate with each other such as, for example, a wired network communication protocol (e.g., TCP/IP), a wireless network communication protocol (e.g., Wi-Fi, WiMAX), a cellular communication protocol (e.g., Wideband Code Division Multiple Access (W-CDMA)), and/or other communication protocols. As such, the network 202 may include any number of additional devices, such as additional computers, routers, and switches, to facilitate communications between the processing device 402 and the server 420.

Figure 5:
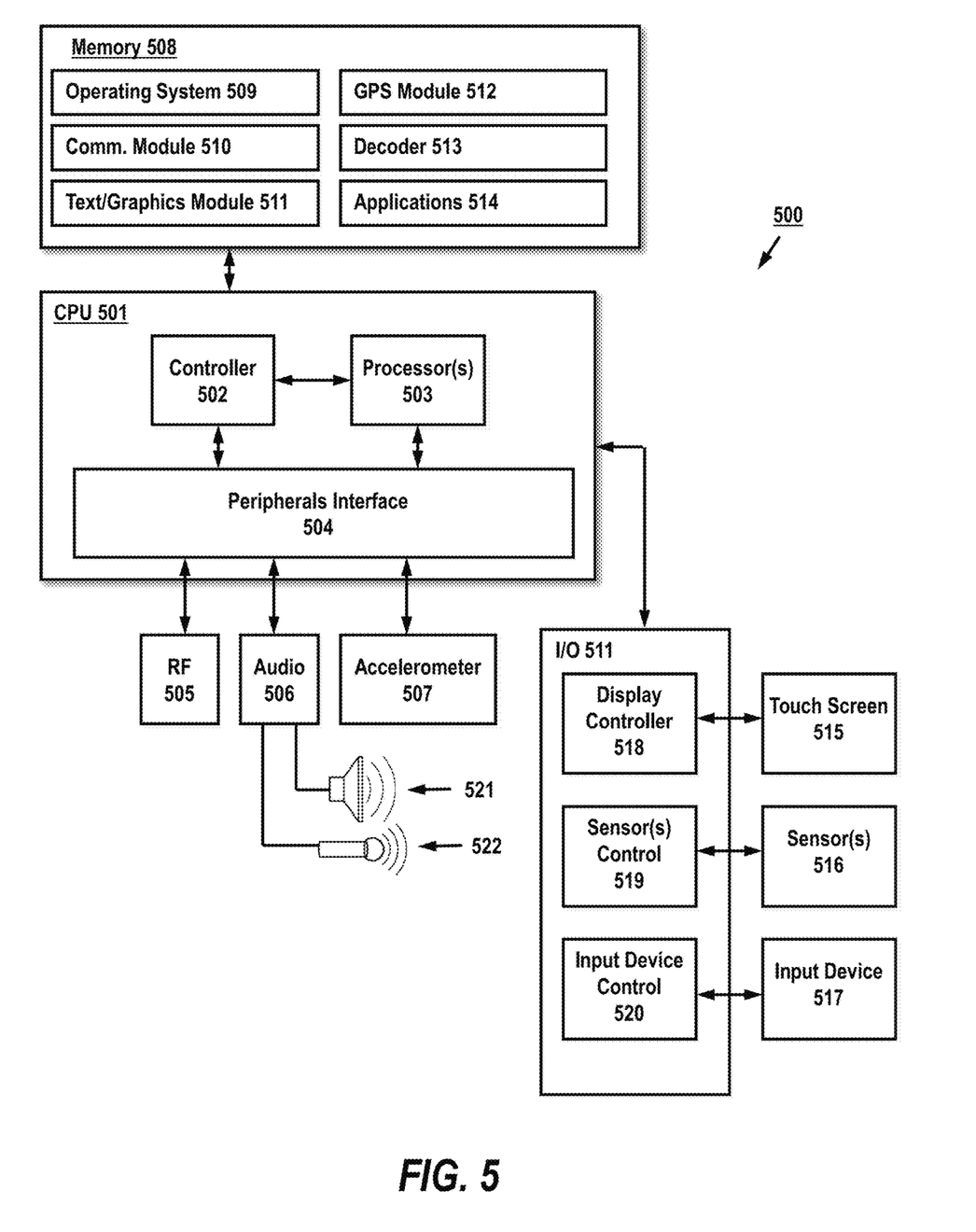
FIG. 5 schematically illustrates an operating environment for a processing device configured to perform e-prescription medical data processing and authentication under an illustrative embodiment.

FIG. 5 is an exemplary embodiment of a computing device 500 (such as processing devices 302, 310), and may be a personal computer, smart phone, tablet computer, laptop and the like. Device 500 may include a central processing unit (CPU) 501 (which may include one or more computer readable storage mediums), a memory controller 502, one or more processors 503, a peripherals interface 504, RF circuitry 505, audio circuitry 506, accelerometer 507, speaker 521, microphone 522, and input/output (I/O) subsystem 221 having display controller 518, control circuitry for one or more sensors 519 and input device control 520. These components may communicate over one or more communication buses or signal lines in device 500. It should be appreciated that device 500 is only one example of a portable multifunction device, and that device 500 may have more or fewer components than shown, may combine two or more components, or a may have a different configuration or arrangement of the components. The various components shown in FIG. 5 may be implemented in hardware or a combination of hardware and software, including one or more signal processing and/or application specific integrated circuits.

Memory (or storage) 508 may include high-speed random access memory (RAM) and may also include non-volatile memory, such as one or more magnetic disk storage devices, flash memory devices, or other non-volatile solid-state memory devices. Access to memory 508 by other components of the device 500, such as processor 503, and peripherals interface 504, may be controlled by the memory controller 502. Peripherals interface 504 couples the input and output peripherals of the device to the processor 503 and memory 508. The one or more processors 503 run or execute various software programs and/or sets of instructions stored in memory 508 to perform various functions for the device 500 and to process data. In some embodiments, the peripherals interface 504, processor(s) 503, decoder 513 and memory controller 502 may be implemented on a single chip, such as a chip 501. In other embodiments, they may be implemented on separate chips.

RF (radio frequency) circuitry 505 receives and sends RF signals, also known as electromagnetic signals. The RF circuitry 505 converts electrical signals to/from electromagnetic signals and communicates with communications networks and other communications devices via the electromagnetic signals. The RF circuitry 505 may include well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. RF circuitry 505 may communicate with networks, such as the Internet, also referred to as the World Wide Web (WWW), an intranet and/or a wireless network, such as a cellular telephone network, a wireless local area network (LAN) and/or a metropolitan area network (MAN), and other devices by wireless communication. The wireless communication may use any of a plurality of communications standards, protocols and technologies, including but not limited to Global System for Mobile Communications (GSM), Enhanced Data GSM Environment (EDGE), high-speed downlink packet access (HSDPA), wideband code division multiple access (W-CDMA), code division multiple access (CDMA), time division multiple access (TDMA), Bluetooth, Wireless Fidelity (Wi-Fi) (e.g., IEEE 802.11a, IEEE 802.11b, IEEE 802.11g and/or IEEE 802.11n), voice over Internet Protocol (VoIP), Wi-MAX, a protocol for email (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), and/or Instant Messaging and Presence Service (IMPS)), and/or Short Message Service (SMS)), or any other suitable communication protocol, including communication protocols not yet developed as of the filing date of this document.

Audio circuitry 506, speaker 521, and microphone 522 provide an audio interface between a user and the device 500. Audio circuitry 506 may receive audio data from the peripherals interface 504, converts the audio data to an electrical signal, and transmits the electrical signal to speaker 521. The speaker 521 converts the electrical signal to human-audible sound waves. Audio circuitry 506 also receives electrical signals converted by the microphone 521 from sound waves, which may include utterances from a speaker. The audio circuitry 506 converts the electrical signal to audio data and transmits the audio data to the peripherals interface 504 for processing. Audio data may be retrieved from and/or transmitted to memory 508 and/or the RF circuitry 505 by peripherals interface 504. In some embodiments, audio circuitry 506 also includes a headset jack for providing an interface between the audio circuitry 506 and removable audio input/output peripherals, such as output-only headphones or a headset with both output (e.g., a headphone for one or both ears) and input (e.g., a microphone).

I/O subsystem 511 couples input/output peripherals on the device 500, such as touch screen 515, sensors 516 and other input/control devices 517, to the peripherals interface 504. The I/O subsystem 221 may include a display controller 518, sensor controllers 519, and one or more input controllers 520 for other input or control devices. The one or more input controllers 520 receive/send electrical signals from/to other input or control devices 517. The other input/control devices 517 may include physical buttons (e.g., push buttons, rocker buttons, etc.), dials, slider switches, joysticks, click wheels, and so forth. In some alternate embodiments, input controller(s) 520 may be coupled to any (or none) of the following: a keyboard, infrared port, USB port, and a pointer device such as a mouse, an up/down button for volume control of the speaker 521 and/or the microphone 522. Touch screen 515 may also be used to implement virtual or soft buttons and one or more soft keyboards.

Touch screen 515 provides an input interface and an output interface between the device and a user. Display controller 518 receives and/or sends electrical signals from/to the touch screen 515. Touch screen 515 displays visual output to the user. The visual output may include graphics, text, icons, video, and any combination thereof. In some embodiments, some or all of the visual output may correspond to user-interface objects. Touch screen 515 has a touch-sensitive surface, sensor or set of sensors that accepts input from the user based on haptic and/or tactile contact. Touch screen 515 and display controller 518 (along with any associated modules and/or sets of instructions in memory 508) detect contact (and any movement or breaking of the contact) on the touch screen 515 and converts the detected contact into interaction with user-interface objects (e.g., one or more soft keys, icons, web pages or images) that are displayed on the touch screen. In an exemplary embodiment, a point of contact between a touch screen 515 and the user corresponds to a finger of the user. Touch screen 515 may use LCD (liquid crystal display) technology, or LPD (light emitting polymer display) technology, although other display technologies may be used in other embodiments. Touch screen 515 and display controller 518 may detect contact and any movement or breaking thereof using any of a plurality of touch sensing technologies now known or later developed, including but not limited to capacitive, resistive, infrared, and surface acoustic wave technologies, as well as other proximity sensor arrays or other elements for determining one or more points of contact with a touch screen 515.

Device 500 may also include one or more sensors 516 that may include a biometric capture device. Sensors 516 may also include additional sensors, such as heart rate sensors, touch sensors, optical sensors that comprise charge-coupled device (CCD) or complementary metal-oxide semiconductor (CMOS) phototransistors that are part of an image capturing device, such as 340, 342. The optical sensor may capture still images or video, where the sensor is operated in conjunction with touch screen display 515. In some illustrative embodiments, there images may also be used for image processing, as described herein. Device 500 may also include one or more accelerometers 507, which may be operatively coupled to peripherals interface 504. Alternately, the accelerometer 507 may be coupled to an input controller 520 in the I/O subsystem 221. The accelerometer is preferably configured to output accelerometer data in the x, y, and z axes.

In some illustrative embodiments, the software components stored in memory 508 may include an operating system 509, a communication module 510, a text/graphics module 511, a Global Positioning System (GPS) module 512, decoder 513 and applications 514. Operating system 509 (e.g., Darwin, RTXC, LINUX, UNIX, OS X, WINDOWS, or an embedded operating system such as VxWorks) includes various software components and/or drivers for controlling and managing general system tasks (e.g., memory management, storage device control, power management, etc.) and facilitates communication between various hardware and software components. Communication module 510 facilitates communication with other devices over one or more external ports and also includes various software components for handling data received by the RF circuitry 505. An external port (e.g., Universal Serial Bus (USB), Firewire, etc.) may be provided and adapted for coupling directly to other devices or indirectly over a network (e.g., the Internet, wireless LAN, etc.).

Text/graphics module 511 includes various known software components for rendering and displaying graphics on the touch screen 515, including components for changing the intensity of graphics that are displayed. As used herein, the term "graphics" includes any object that can be displayed to a user, including without limitation text, web pages, icons (such as user-interface objects including soft keys), digital images, videos, animations and the like. Additionally, soft keyboards may be provided for entering text in various applications requiring text input. GPS module 512 determines the location of the device and provides this information for use in various applications. Applications 514 may include various modules, including authentication modules, prescription modules, health monitoring software, sensor software, navigation software, mapping, address books/contact list, email, instant messaging, and the like. In some illustrative embodiments, Applications 514 may communicate with sensors 516, configured as a biometric capture device.

Figure 6:
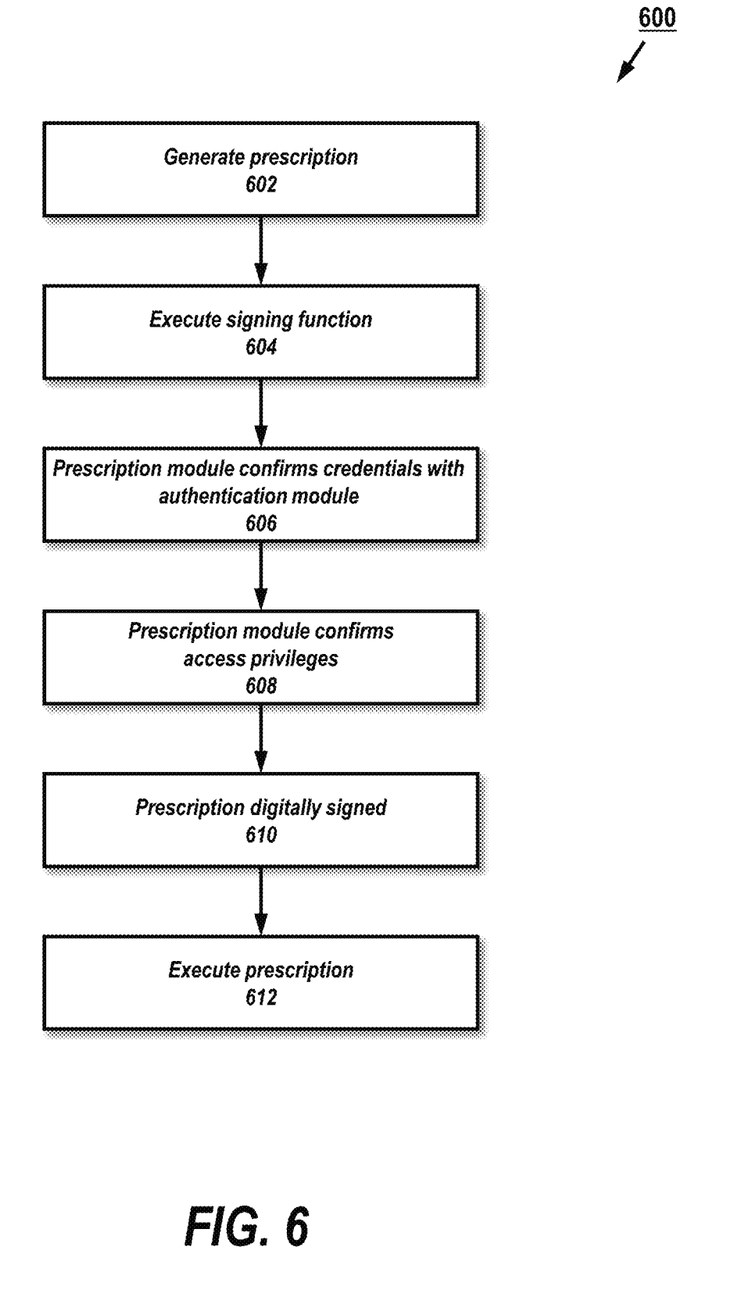
FIG. 6 shows simplified process for generating, authenticating and executing an e-prescription under an illustrative embodiment.

FIG. 6 shows simplified process 600 for generating, authenticating and executing an e-prescription under an illustrative embodiment. In block 602, a processing device (e.g., 310), which may be configured as part of a clinical system (e.g., 208) generates a prescription, which, in this example, comprises one or more prescriptions for a controlled substance. When the prescription is generated, the prescriber may review the prescriptions an indicate on the processing device which prescriptions are ready to be electronically signed. Once the indication is entered, the processing device executes an electronic signing function in block 604. In some illustrative embodiments, the signing includes a two-factor authentication protocol, where the prescriber is required to entry a plurality of authentication tokens. One token may comprise an identification token, which may comprise data identifying the prescriber. This identification token may be an alphanumeric password known only to the prescriber, or may alternately or in addition include other identifying tokens, such as biometric data and the like. Another token may comprise an OTP that is provided to another processing device (e.g., 302), and then entered into the first processing device (e.g., 310).

Once the processing device (e.g., via 414) confirms the entries, a prescription module confirms the credentials in block 606 and confirms access privileges in block 608. The authentication module verified that the authentication tokens the prescriber entered correspond to the credentials (tokens) associated with the prescriber's account. This correspondence may me established at the time the credentials for the account created and issued to the prescriber. The access control verifies that the user account to which the prescriber authenticated via the two-factor protocols includes the access privileges for controlled substances. In other words, the prescriber must be authorized by the computer network system's security controls to execute the signing function for such prescriptions. The assignment of access privilege may be specified during a device registration process to configure logical access controls for user accounts on the computer network system, based on predetermined authorization policies and processes. The process 600 then allows the processing device to digitally sign the prescription in block 610, wherein the prescription may be executed in block 612 and transmitted to other portions of the computer network system for fulfillment and/or monitoring (e.g., 204, 210).

Figure 7:
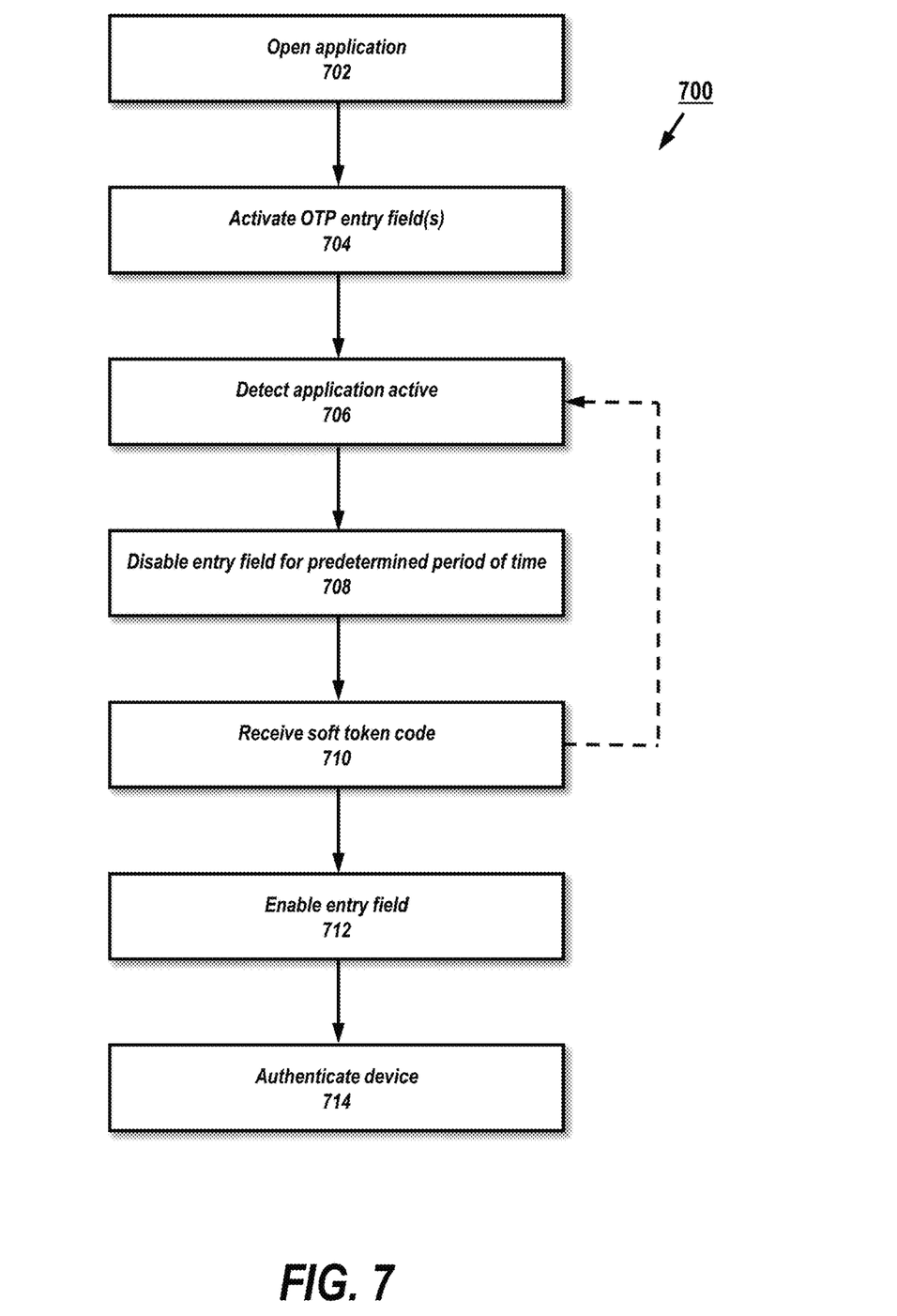
FIG. 7 shows a simplified process for utilizing a device application to secure and authenticating a device for e-prescription access under an illustrative embodiment.

FIG. 7 shows a simplified process 700 for utilizing a device application to secure and authenticating a device for e-prescription access under an illustrative embodiment. In this example, the process presumes that a computer network system is configured to disallow a device to generate and/or receive an OTP, while entering the OTP on the same device. Such a configuration may be advantageous to minimize security issues, particularly where an unauthorized individual having access to an OTP service gains access to the prescription system. In block 702, a user of a processing device (e.g., 310) opens a prescription application on that device. Next, the processing device activates OTP entry fields for the prescription application in block 704. At that point the processing device determines is the opened application from block 702 is active in block 706. In some illustrative embodiments, the processing device is configured to detect through the operating system whether the opened application is deactivated (e.g., closed, minimized, backgrounded, etc.). In some illustrative embodiments, deactivation may include multitasking, where the prescription application shares resources in the operating system with other open applications. At this time, the OTP entry fields are disabled for a predetermined period of time (e.g., 30 seconds, 60 seconds, etc.) in order to allow any existing time-based OTPs to expire.

The processing device may then receive one or more soft token codes during the predetermined period of time in block 710, wherein the soft token code is received on another processing device (e.g., 302). If the processing device determines that the application has been deactivated during the period of time (shown by dotted arrow), the process 700 may continue disabling the entry field and reset the disablement time period to again clear out the existing OTP and begin a new time count. If the time period has expired and the processing device continues to detect that the application is active, the processing device activates or enables the entry field for the prescription application in block 712, wherein the processing device may be authenticated in block 714. In one example, if a prescription application is determined to be deactivated in a single session (e.g., during continuous entry attempt of prescription data for one or more patients) and is subsequently determined to be reactivated, the authentication module continues disabling the entry field and starts a new timer of a predetermined period of time. After the predetermined period of time has passed, the authentication module then enables the entry field for the OTP for the prescription module. As mentioned above, the authentication module may be configured to determine device multitasking a deactivation condition. In some illustrative embodiments, the authentication module may require device full-screen control of the prescription application, where multi-window modes are prohibited. This may be detected by the authentication module, but may alternately or additionally be incorporated into the prescription module, where full-screen control must be activated before the prescription module is allowed to be executed.

Figure 8:
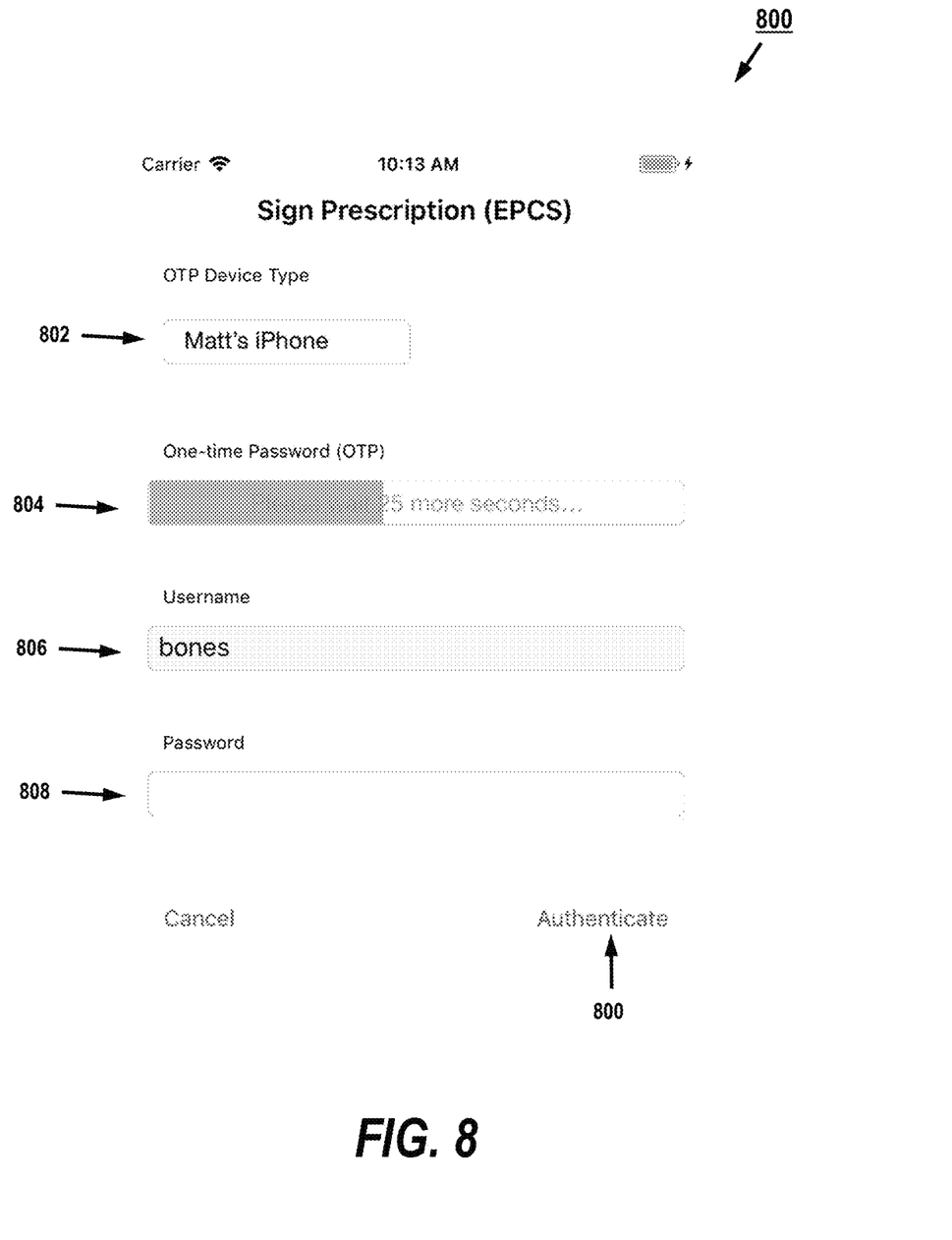
FIG. 8 shows a simulated authentication sign in screen for a processing device for prescribing controlled substances under an illustrative embodiment.

FIG. 8 shows a simulated authentication sign in screen 800 for a processing device (e.g., 802, 810) for prescribing controlled substances under an illustrative embodiment. In this example, a device identification entry field 802 allows a user to enter device identification data, while a user name may be entered in field 806. These entries may be made, for example, after the OTP entry fields are activated as in block 704 of FIG. 7. After the application is determined as active (see 706), the entry field for the password is disabled and OTP status identifier 804 indicates a period of time in which the user has to wait. Once a soft token code is received on another device, that code may be entered in field 808, and the user may be authenticated after activating icon 800.

The figures and descriptions provided herein may have been simplified to illustrate aspects that are relevant for a clear understanding of the herein described devices, structures, systems, and methods, while eliminating, for the purpose of clarity, other aspects that may be found in typical similar devices, systems, and methods. Those of ordinary skill may thus recognize that other elements and/or operations may be desirable and/or necessary to implement the devices, systems, and methods described herein. But because such elements and operations are known in the art, and because they do not facilitate a better understanding of the present disclosure, a discussion of such elements and operations may not be provided herein. However, the present disclosure is deemed to inherently include all such elements, variations, and modifications to the described aspects that would be known to those of ordinary skill in the art.

Exemplary embodiments are provided throughout so that this disclosure is sufficiently thorough and fully conveys the scope of the disclosed embodiments to those who are skilled in the art. Numerous specific details are set forth, such as examples of specific components, devices, and methods, to provide this thorough understanding of embodiments of the present disclosure. Nevertheless, it will be apparent to those skilled in the art that specific disclosed details need not be employed, and that exemplary embodiments may be embodied in different forms. As such, the exemplary embodiments should not be construed to limit the scope of the disclosure. In some exemplary embodiments, well-known processes, well-known device structures, and well-known technologies may not be described in detail.

The terminology used herein is for the purpose of describing particular exemplary embodiments only and is not intended to be limiting. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The steps, processes, and operations described herein are not to be construed as necessarily requiring their respective performance in the particular order discussed or illustrated, unless specifically identified as a preferred order of performance. It is also to be understood that additional or alternative steps may be employed.

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on," "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another element, component, region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the exemplary embodiments.

The disclosed embodiments may be implemented, in some cases, in hardware, firmware, software, or any tangibly-embodied combination thereof. It is understood by those skilled in the art that the present disclosure do The disclosed embodiments may also be implemented as instructions carried by or stored on one or more non-transitory machine-readable (e.g., computer-readable) storage medium, which may be read and executed by one or more processors. A machine-readable storage medium may be embodied as any storage device, mechanism, or other physical structure for storing or transmitting information in a form readable by a machine (e.g., a volatile or non-volatile memory, a media disc, or other media device).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

In the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment.

What is claimed is:

1. An apparatus for processing and securing prescription data on a computer network, comprising:
   a processor;
   a memory, operatively coupled to the processor;
   a communications interface, operatively coupled to the processor, wherein the communications interface is configured to communicate with the computer network;
   a prescription module, operatively coupled to the processor, wherein the prescription module is configured to activate a prescription application to register prescription data after a user has been authenticated for the prescription application; and
   an authentication module, operatively coupled to the processor, wherein the authentication module is configured to
      automatically disable an entry field in the prescription application, for a predetermined period of time after the user authentication during a registration of the prescription data from the apparatus, wherein the registration comprises the generation of a new prescription comprising the prescription data,
      determine, while the entry field is disabled, that the prescription application has not been deactivated during the predetermined period of time during the registration of the prescription data,
      transmit, while the entry field is disabled, a one-time password comprising a soft token code that is associated with the user authentication during the registration of the prescription data, to a device other than the apparatus executing the authentication module;
      activate the entry field in the prescription application after the one-time password has been transmitted, and after the predetermined period of time has lapsed,
      receive entry of the on-time password in the activated entry field, and
      secondarily authenticate the registration of the prescription data using the one-time password for the new prescription.

2. The apparatus of claim 1, wherein the authentication module is configured to determine if the prescription application is active by determining if the prescription application is closed, minimized or backgrounded.

3. The apparatus of claim 1, wherein the authentication module is configured to continue disabling the entry field in the prescription application for a new predetermined period of time if the authentication application determines the prescription application is not active.

4. The apparatus of claim 1, wherein the processor is configured to transmit the authenticated registered prescription data to a pharmacy computer system of the computer network.

5. The apparatus of claim 4, wherein the transmitted authenticated registered prescription data is configured to be further authenticated by an authentication service server communicatively coupled to the pharmacy computer system.

6. The apparatus of claim 1, wherein the prescription data comprises data relating to a controlled substance.

7. A processor-based method for securing prescription data on an apparatus communicating with a computer network, comprising:
   activating a prescription module, via a processor, for registering prescription data after a user has been authenticated the prescription application;
   activating an authentication module, via the processor;
   automatically disabling, via the authentication module, an entry field in the prescription application after the user authentication during the registration of the prescription data, for a predetermined period of time;
   determining, via the authentication module, while the entry field is disabled, that the prescription application has not been deactivated during the registration of the prescription data from the processor for the predetermined period of time, wherein the registration comprises the generation of a new prescription comprising the prescription data;
   transmitting, while the entry field is disabled, a one-time password comprising a soft token code that is associated with the user authentication during the registration of the prescription data, to a device other than the apparatus executing the authentication module;
   activating, via the authentication module, the entry field in the prescription application after transmitting the one-time password, and after the predetermined period of time has lapsed;
   receiving in the authentication module, entry of the one-time password in the activated entry field; and
   secondarily authenticating, via the authentication module, the registration of the prescription data using the one-time password for the new prescription.

8. The processor-based method of claim 7, wherein determining if the prescription application is active comprises determining if the prescription application is closed, minimized or backgrounded.

9. The processor-based method of claim 7, further comprising continue disabling, via the authentication module, the entry field in the prescription application for a new predetermined period of time if the authentication application determines the prescription application is not active.

10. The processor-based method of claim 7, further comprising transmitting, via a communications interface, the authenticated registered prescription data to a pharmacy computer system of the computer network.

11. The processor-based method of claim 10, wherein transmitting the authenticated registered prescription data comprises configuring the authentication registered prescription data for further authentication by an authentication service server communicatively coupled to the pharmacy computer system.

12. The processor-based method of claim 7, wherein the prescription data comprises data relating to a controlled substance.

13. A processor-based method for securing prescription data on an apparatus communicating with a computer network, comprising:
- activating a prescription module, via a processor, for registering prescription data after a user has been authenticated for the prescription application, wherein the registering comprises the generation of a new prescription from the processor comprising the prescription data;
- activating an authentication module, via the processor;
- automatically disabling, via the authentication module, an entry field in the prescription application after user authentication during the registering of the prescription data, for a predetermined period of time;
- determining, via the authentication module, while the entry field is disabled, that the prescription application has not been deactivated during the registering of the prescription data during the predetermined period of time;
- transmitting, while the entry field is disabled, a one-time password comprising a soft token code that is associated with the user authentication during the registration of the prescription data, to a device other than the apparatus executing the authentication module;
- activating, via the authentication module, the entry field in the prescription application after the one-time password has been transmitted, and after the predetermined period of time has lapsed;
- receiving, in the authentication module, entry of the one-time password in the activated entry field; and
- secondarily authenticating, via the authentication module the registering of the prescription data using the one-time password for the new prescription.

14. The processor-based method of claim 13, wherein determining if the prescription application is active comprises determining if the prescription application is closed, minimized or backgrounded.

15. The processor-based method of claim 13, further comprising continue disabling, via the authentication module, the entry field in the prescription application for a new predetermined period of time if the authentication application determines the prescription application is not active.

16. The processor-based method of claim 13, further comprising transmitting, via a communications interface, the authenticated registered prescription data to a pharmacy computer system of the computer network.

17. The processor-based method of claim 16, wherein transmitting the authenticated registered prescription data comprises configuring the authentication registered prescription data for further authentication by an authentication service server communicatively coupled to the pharmacy computer system.

18. The processor-based method of claim 13, wherein the prescription data comprises data relating to a controlled substance.

* * * * *